(12) United States Patent
Bauer

(10) Patent No.: US 7,662,135 B2
(45) Date of Patent: Feb. 16, 2010

(54) METHODS AND APPARATUS FOR CONTROLLING INTRAVENOUS FLUID FLOW TO A PATIENT

(76) Inventor: Byron Cris Bauer, 18711 County Road 1140, St. James, MO (US) 65559

( * ) Notice: Subject to any disclaimer, the term of this patent is extended or adjusted under 35 U.S.C. 154(b) by 96 days.

(21) Appl. No.: 10/264,032

(22) Filed: Oct. 3, 2002

(65) Prior Publication Data

US 2004/0068237 A1  Apr. 8, 2004

(51) Int. Cl.
*A61M 5/14* (2006.01)
(52) U.S. Cl. .................. 604/251; 604/247; 604/254
(58) Field of Classification Search .......... 604/80, 604/81, 246, 247, 248, 251, 254, 255, 257, 604/258, 85, 414
See application file for complete search history.

(56) References Cited

U.S. PATENT DOCUMENTS

| | | | |
|---|---|---|---|
| 3,216,418 A * | 11/1965 | Scislowicz .............. 604/80 |
| 3,298,367 A * | 1/1967 | Bergman .............. 604/246 |
| 3,927,693 A * | 12/1975 | Johnston .............. 137/625.47 |
| 4,250,879 A * | 2/1981 | Muetterties .............. 604/81 |
| 4,534,758 A * | 8/1985 | Akers et al. .............. 604/85 |
| 4,573,974 A | 3/1986 | Ruschke |
| 4,601,712 A | 7/1986 | Cole et al. |
| 4,681,606 A | 7/1987 | Swan, Jr. et al. |
| 5,057,090 A | 10/1991 | Bessman |
| 5,279,557 A | 1/1994 | Lomick |
| 5,776,109 A | 7/1998 | Urrutia |
| 5,910,135 A | 6/1999 | Hadzic et al. |
| 5,916,201 A * | 6/1999 | Wilson et al. .............. 604/248 |
| 6,099,512 A | 8/2000 | Urrutia |
| 6,261,267 B1 | 7/2001 | Chen |

* cited by examiner

*Primary Examiner*—Kevin C Sirmons
*Assistant Examiner*—Phillip Gray
(74) *Attorney, Agent, or Firm*—Armstrong Teasdale LLP

(57) ABSTRACT

An apparatus regulates fluid flow supplied to a patient through an intravenous infusion system. The apparatus includes a first fluid passageway, a second fluid passageway, an inlet, and a control device. The first fluid passageway is for discharging fluid therefrom at a first predetermined rate of flow. The second fluid passageway is for discharging fluid therefrom at a second predetermined rate of flow, wherein the second predetermined rate of flow is different than the first predetermined rate of flow. The inlet is in flow communication with the first and second fluid passageways. The control device is between the inlet and the first and second fluid passageways, and is variably positionable for controlling fluid flow into the first and second fluid passageways.

31 Claims, 3 Drawing Sheets

METHODS AND APPARATUS FOR CONTROLLING INTRAVENOUS FLUID FLOW TO A PATIENT

BACKGROUND OF THE INVENTION

This invention relates generally to intravenous infusion systems, and more particularly to a drip chamber for use with intravenous infusion systems.

At least some known intravenous infusion systems include a fluid reservoir connected via a series of conduits to a needle, which is inserted into a vein of a patient for supplying fluids intravenously to the patient. A drip chamber positioned between the fluid reservoir and the needle allows medical personnel to monitor and control a rate of fluid flow supplied to the patient. The drip chamber includes an internal valve that permits fluid flow to be supplied therethrough at a predetermined rate. The drip chamber provides a means of measuring the delivery volume supplied to the patient. Each drip chamber is classified in drops per milliliter (mL), such that a certain number of drops equals one mL of fluid.

During administration of intravenous fluids, it may be necessary to vary a rate of flow through the system. For example, a relatively low delivery flow rate, such as 60 drops/mL, may be desirable for administration of fluids in a moderate, continuous flow. However, a higher delivery flow rate, such as 10 drops/mL, may be necessary in emergent situations, for example when quick delivery of large fluid boluses or faster infusion rates becomes necessary to support the patient's circulation.

To facilitate supplying fluid at different delivery flow rates to a patient, at least some known systems include two drip chambers coupled within the system. A particular drip chamber may be selected by using a series of clamps or valves coupled downstream from the drip chamber, or by manually exchanging one drip chamber for another. In at least some other known systems, varying the predetermined delivery flow rate of the system requires replacing a currently attached drip chamber rated at a first delivery flow rate with a drip chamber rated at a second delivery flow rate.

BRIEF DESCRIPTION OF THE INVENTION

In one aspect, an apparatus for regulating fluid flow supplied to a patient through an intravenous infusion system is provided. The apparatus includes a first body portion, a second body portion, an inlet, and a control device. The first body portion is for discharging fluid therefrom at a first predetermined rate of flow. The second body portion is for discharging fluid therefrom at a second predetermined rate of flow, wherein the second predetermined rate of flow is different than the first predetermined rate of flow. The inlet is in flow communication with the first and second body portions. The control device is between the inlet and the first and second body portions, and is variably positionable for controlling fluid flow into the first and second body portions.

In another aspect of the invention, an infusion system for administering intravenous fluid to a patient is provided. The infusion system includes a fluid reservoir and a drip chamber that is coupled in flow communication to the fluid reservoir. The drip chamber includes a first body portion, a second body portion, a control device, and an inlet coupled in flow communication to the first and second body portions. The control device is variably positionable for controlling fluid flow from the inlet into the first and second body portions. The first body portion is for discharging fluid from the drip chamber at a first predetermined rate of flow, and the second body portion is for discharging fluid from the drip chamber at a second predetermined rate of flow.

In a further aspect, a method for administering intravenous fluid to a patient is provided. The method comprises coupling a drip chamber including a first body portion and a second body portion to a fluid reservoir, channeling fluid flow from the fluid reservoir to the drip chamber inlet, positioning a control device to control fluid flow discharged from the drip chamber inlet, and channeling fluid flow from the drip chamber inlet to at least one of the first body portion and a second body portion, wherein the first body portion is configured to discharge fluid therefrom at a first predetermined flow rate, and the second body portion is configured to discharge fluid therefrom at a second predetermined flow rate that is different than the first predetermined flow rate.

In yet another aspect of the invention, a method for fabricating a drip chamber for use in supplying intravenous fluids at a controlled flow rate is provided. The method comprises forming a bifurcated chamber including a first body portion and a second body portion, wherein the first body portion is configured to discharge fluids at a first predetermined flow rate, the second body portion is configured to discharge at a second predetermined flow rate that is different than the first predetermined flow rate, coupling a control device to the bifurcated chamber, coupling the bifurcated chamber to an inlet that is in flow communication with the first and second body portions, wherein the control device controls fluid flow into the first and second body portions, and coupling the bifurcated chamber to an outlet that is in flow communication with the first and second body portions.

DETAILED DESCRIPTION OF THE INVENTION

Figure 1:
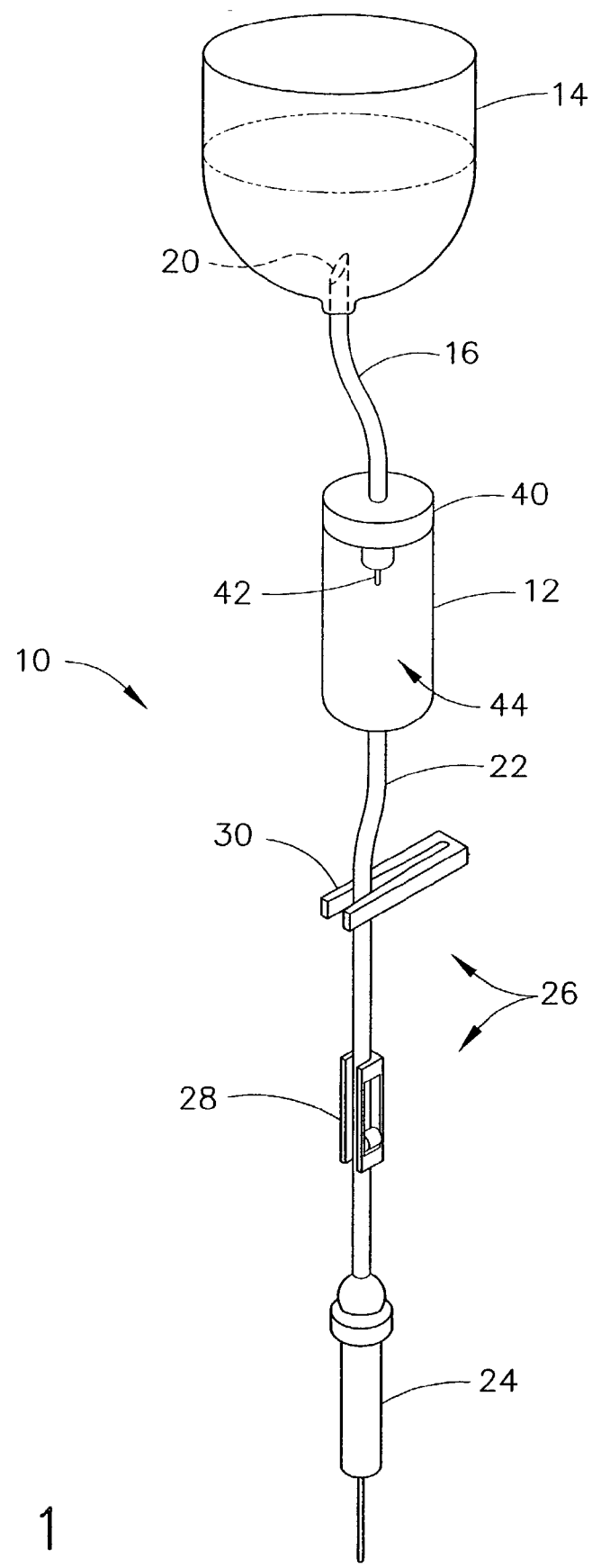
FIG. 1 is an illustration of an exemplary intravenous infusion system including a known drip chamber.

FIG. 1 is an exemplary illustration of an intravenous infusion system 10 including a known drip chamber 12. In one embodiment, intravenous infusion system 10 is substantially similar to Continu-Flo® Solution Set, commercially available from Baxter Healthcare Corporation, Deerfield, Ill. 60015. Intravenous infusion system 10 includes a reservoir 14 which stores intravenous fluid and is coupled in flow communication to drip chamber 12 by a fluid passageway 16. More specifically, reservoir 14 is positioned at a higher elevation than that of drip chamber 12 to enable gravitational force to cause fluid to be discharged from reservoir 14. In the exemplary embodiment, passageway 16 includes a sharpened inlet 20, known as a spike, for piercing fluid reservoir 14 such that drip chamber 12 is coupled in flow communication to fluid reservoir 14.

In the exemplary embodiment, drip chamber 12 is in turn coupled in flow communication by tubing 22 to a-needle 24, which may be inserted into a vein of a patient for administration of intravenous fluids. In one embodiment, tubing 22 is substantially transparent, flexible, and compressible. A plurality of flow regulating devices 26 are attached to tubing 22 downstream from drip chamber 12 and upstream from needle 24. Flow regulating devices 26 are used to regulate or stop the flow of intravenous fluid through tubing 22 to needle 24. For example, in the exemplary embodiment, system 10 includes at least one roller clamp 28 that is clamped to tubing 22 such that moving the roller along tubing 22 adjusts a rate of fluid flow through tubing 22. In another embodiment, system 10 includes at least one slide clamp 30 which when moved will completely occlude tubing 22 to prevent fluid flow therethrough.

Drip chamber 12 includes a cap 40, a flow metering valve 42, and a hollow chamber 44. Cap 40 includes an inlet 46 extending therethrough in flow communication with chamber 44. Chamber 44 is formed of a clear material to enable timing and counting of drops of fluid therethrough for verifying the flow rate from flow metering valve 42. Flow metering valve 42 is formed integrally with cap 40 and permits fluid flow to be supplied therethrough into chamber 44 at a predetermined rate. Specifically, each drip chamber 12 is classified in drops per milliliter (mL), such that a certain number of drops discharged therethrough equals one mL of fluid.

Figure 2:
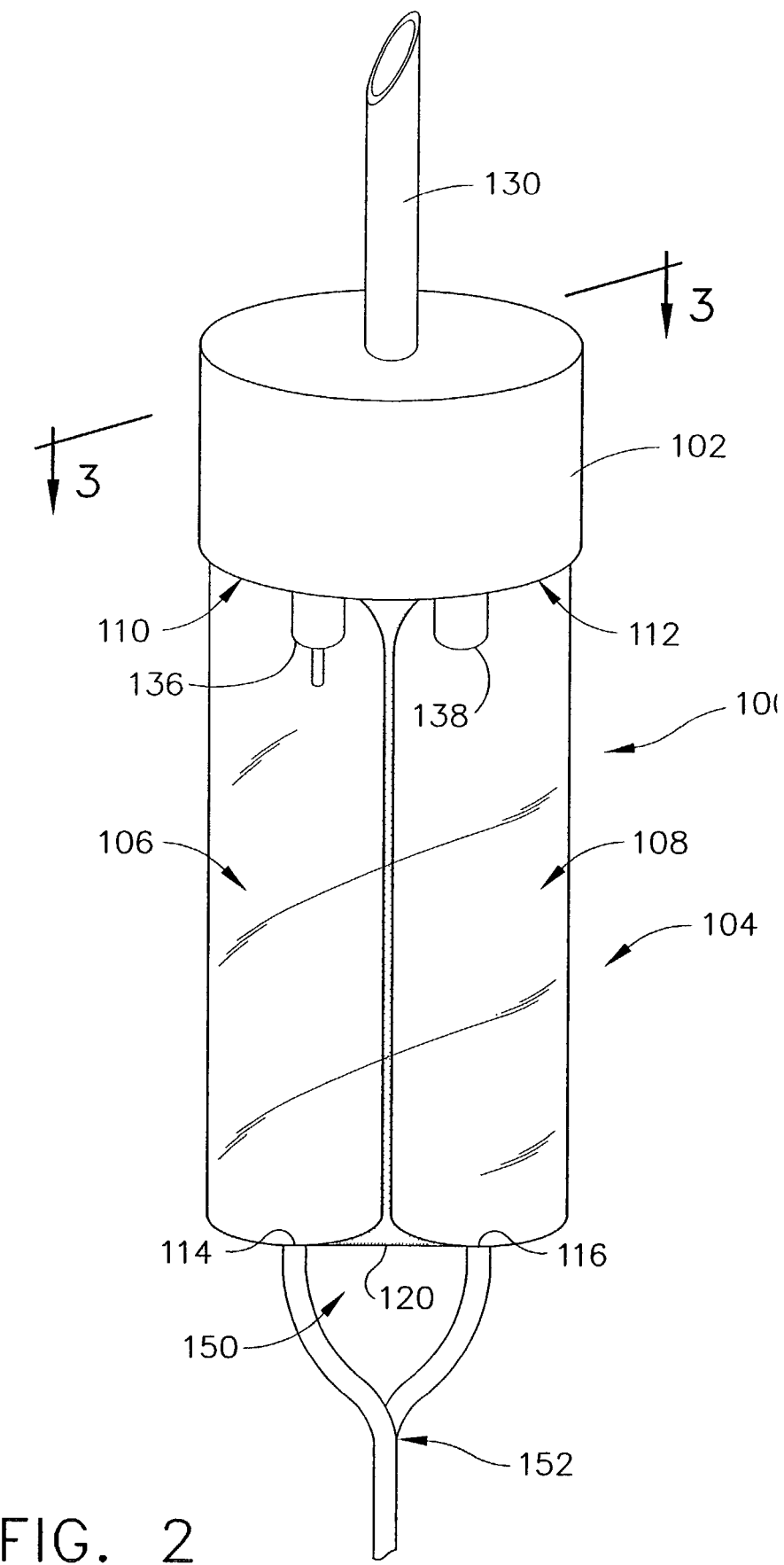
FIG. 2 is a side view of a drip chamber that may be used with the intravenous infusion system shown in FIG. 1.
Figure 3:
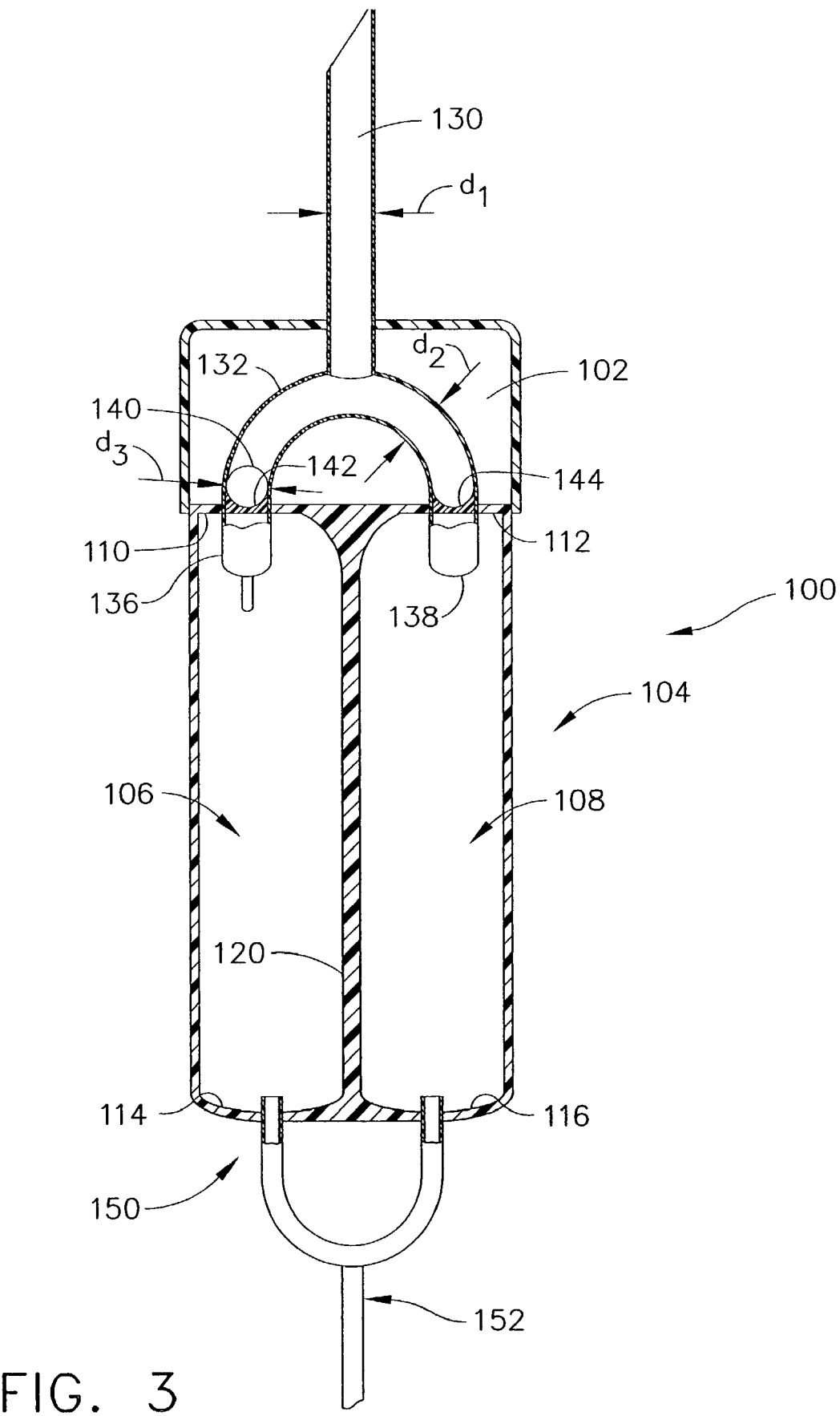
FIG. 3 is a cross-sectional view of the drip chamber shown in FIG. 2 and taken along line 3-3.

FIG. 2 is a side view of an exemplary drip chamber 100 that may be used with an intravenous infusion system, such as intravenous infusion system 10 (shown in FIG. 1). FIG. 3 is a cross-sectional view of drip chamber 100 taken along line 3-3. In the exemplary embodiment, drip chamber 100 includes a cap 102, and a bifurcated chamber 104. In an alternative embodiment, chamber 104 is non-bifurcated and is a single chamber. Chamber 104 includes a first body portion 106 and a second body portion 108. Each body portion 106 and 108 includes a bore extending therethrough from a respective inlet end 110 and 112, to a respective outlet end 114 and 116.

In the exemplary embodiment, each body portion 106 and 108 is fabricated from a clear material, and each respective body portion 106 and 108 has a substantially circular cross-sectional profile. Furthermore, in the exemplary embodiment body portion 106 and 108 are coupled such that a contoured wall 120 extends therebetween along each body portion 106 and 108. In another embodiment, drip chamber 100 does not include wall 120 and rather chamber 106 and 108 are in direct contact.

Cap 102 extends over chamber 104 in sealing contact with chamber 104. Cap 102 includes an inlet 130 through cap 102 into a fluid passageway 132 defined within cap 102. In the exemplary embodiment, fluid passageway 132 is formed integrally within cap 102. In another embodiment, fluid passageway 132 is formed into cap 102. Fluid passageway 132 couples inlet 130 in flow communication with each chamber body portion 106 and 108. More specifically, fluid passageway 132 couples inlet 130 in flow communication with a pair of flow metering valves 136 and 138 that extend into each chamber body portion 106 and 108.

Metering valves 136 and 138 are substantially similar to flow metering valve 42 (shown in FIG. 1) and each extends substantially concentrically into each chamber body portion 106 and 108 at each respective body portion inlet end 110 and 112. Metering valves 136 and 138 are each rated to permit fluid flow therethrough into each respective chamber body portion 106 and 108 at a predetermined rate of fluid flow. In an alternative embodiment, chamber 104 is non-bifurcated and both metering valves 136 and 138 permit fluid flow therethrough into the same single chamber. More specifically, in the exemplary embodiment, metering valve 136 is configured to permit fluid flow therethrough at a first predetermined rate of fluid flow and metering valve 138 is configured to permit fluid flow therethrough at a second predetermined rate of fluid flow that is different than the first predetermined rate of fluid flow. In one embodiment, metering valve 136 is sized to permit a delivery fluid flow rate of 60 drops/mL, and metering valve 138 is sized to deliver a higher delivery flow rate, such as 10 drops/mL.

In the exemplary embodiment, fluid passageway 132 is substantially semi-circular and inlet 130 is coupled in flow communication to fluid passageway 132 approximately midway between metering valves 136 and 138. Inlet 130 has a diameter $d_1$ that is smaller than a diameter $d_2$ of fluid passageway 132. A flow control device 140 is positioned within fluid passageway 132 for controlling fluid flow from inlet 130 into chamber 104. Specifically, in the exemplary embodiment, flow control device 140 is a sphere that has a diameter $d_3$ that is slightly smaller than fluid passageway $d_2$. Accordingly, sphere 140 is sized to be in rolling contact within fluid passageway 132.

Fluid passageway 132 also includes a pair of seats 142 and 144 that are immediately upstream from each respective metering valve 136 and 138. Seats 142 and 144 are sized to receive sphere 140 therein in sealing contact to prevent fluid flow into a respective body chamber 106 and 108. In one embodiment, sphere 140 is substantially non-buoyant such that when chamber 100 is in a gravity-feed position such that cap 102 is positioned at a higher elevation than bifurcated chamber 104, sphere forms a seal with either seat 142 or 144 during drip chamber 100 operation.

A position of sphere 140 within fluid passageway 132 is variably selected to control fluid flow into each body chamber 106 and 108, and thus to control a fluid delivery rate of drip chamber 100. Specifically, in the exemplary embodiment, a position of sphere 140 is varied by inverting drip chamber 100 from a gravity feed position towards an upside down position in which cap 102 is positioned at the same elevation or approaching a lower elevation than bifurcated chamber 104. Rotating chamber 104 as such, enables sphere 140 to roll from one seat 142 or 144 towards the other respective seat 144 or 142. Accordingly, as drip chamber 104 is returned to the gravity feed position, the position of sphere 140 with respect to drip chamber 104 is changed, and accordingly, the fluid delivery rate from chamber 104 is also changed. In an alternative embodiment, flow control device 140 includes a dial (not shown) that includes an indicator dial that is rotatably coupled to a stop blank (not shown) positioned within fluid passageway 132. Rotation of the dial changes the position of the blank with respect to chamber body portions 106 and 108. In another alternative embodiment, flow control device 140 includes a flapper valve (not shown) that is selectively movable within fluid passageway 132. In yet another embodiment, flow control device 140 includes a mechanical device that is selectively positionable to obstruct flow into at least one of chamber body portion 106 and chamber body portion 108.

In the exemplary embodiment, drip chamber 100 is formed integrally and is a sealed system between inlet 130 and a drip chamber outlet 150. Specifically, outlet 150 includes a Y-junction 152 that is coupled in flow communication with each chamber body portion 104 and 106. Accordingly, fluid entering either chamber body portion 104 or 106 is discharged from drip chamber 100 through outlet 150.

Under normal operating conditions, inlet 130 is coupled in flow communication to a fluid reservoir, such as reservoir 14 (shown in FIG. 1), such that intravenous fluid flows from reservoir 14 into drip chamber 100 via inlet 130. Fluid then flows into bifurcated chamber 104. More specifically, depending upon a position of sphere 140, fluid flows into either chamber body portion 106 or chamber body portion 108 through fluid passageway 132.

Intravenous fluid is then discharged into chamber body portion 106 or 108 through a respective flow metering valve 136 or 138. The rate at which fluid droplets fall through chamber 104 is predetermined by metering valves 136 or 138 and represents a flow rate of drip chamber 100. Each chamber body portion 106 and 108 is fabricated from a clear material, to permit visual inspection of the drip or flow rate of the intravenous fluid through drip chamber 104.

If a patient becomes unstable, or requires emergent intravenous intervention, chamber 100 is rotated from the gravity feed position as described above, such that sphere 140 is repositioned adjacent a different seat 142 or 144 to change or increase the predetermined flow rate through chamber 100. For example, when sphere 140 is positioned within seat 142, sphere 140 substantially obstructs flow into body chamber 106, and fluid flows through metering valve 138 into body chamber 108. Conversely, when sphere 140 is positioned within seat 144, sphere substantially obstructs flow into body chamber 108, and fluid flows through metering valve 136 into body chamber 106. Because chamber 100 is a sealed system, a risk of contaminants entering drip chamber 100 when a fluid delivery rate is changed is substantially eliminated. Fluid flow entering chamber 104 is discharged through chamber outlet 150.

The above-described drip chamber is cost-effective and highly reliable. The drip chamber is integrally formed to include a bifurcated chamber wherein each body portion within the chamber supplies fluids therefrom at a different predetermined rate of flow. Furthermore, because the control device is positioned between the drip chamber inlet and the bifurcated chamber, the control device is within the sealed system, and as such, changing the flow delivery rate from a first delivery rate of flow to a second delivery rate of flow is a relatively simple procedure in, which the risk of contaminants entering the system is substantially eliminated. Accordingly, the drip chamber enables intravenous fluid flow selection to be completed in a cost-effective and highly reliable manner.

While the invention has been described in terms of various specific embodiments, those skilled in the art will recognize that the invention can be practiced with modification within the spirit and scope of the claims.

What is claimed is:

1. Apparatus for regulating fluid flow supplied to a patient through an intravenous infusion system, said apparatus comprising:
    a first passageway comprising a seat, said first passageway for discharging fluid therefrom at a first predetermined rate of flow when said apparatus is oriented in a first position;
    a second passageway comprising a seat, said second passageway for discharging fluid therefrom at a second predetermined rate of flow, the second predetermined rate of flow different from the first predetermined rate of flow when said apparatus is in the first position, said second passageway in flow communication with said first passageway;
    an inlet coupled in flow communication with said first and second passageways such that fluid discharged from said inlet is received in both said first and second passageways when said apparatus is in the first position in which said inlet is positioned at a higher elevation than at least one of said first and second passageways; and
    a control device which may be selectively positioned in sealing contact against one seat of said first and second passageways only when said apparatus is in the first position, said apparatus is rotated from the first position to a second position such that at least one of said first and second passageways is positioned at a higher elevation than said inlet in order to move said control device from said first passageway seat through said first passageway to said second passageway seat through said second passageway for selectively controlling fluid flow out of said first and second passageways when said apparatus is returned to the first position.

2. Apparatus in accordance with claim 1 wherein said apparatus is unitary.

3. Apparatus in accordance with claim 2 wherein said apparatus is a sealed system, such that said control device is variably positionable without breaching said sealed system.

4. Apparatus in accordance with claim 2 wherein said control device is variably positionable for controlling fluid flow out of said first and second passageways by:
    rotating said apparatus from the first position to the second position; and
    rotating said apparatus from the second position to the first position.

5. Apparatus in accordance with claim 2 wherein said control device is variably positionable for controlling fluid flow out of said first and second body passageways by inverting said apparatus.

6. Apparatus in accordance with claim 2 further comprising a chamber in flow communication with at least one of said first and second passageways, at least a portion of said chamber is transparent.

7. Apparatus in accordance with claim 6 wherein said chamber is bifurcated such that a first chamber portion is in flow communication with said first passageway, and a second chamber portion is in flow communication with said second passageway.

8. Apparatus in accordance with claim 6 wherein said chamber is unitary such that said first passageway and said second passageway are in flow communication with, and discharge fluid into, said chamber.

9. Apparatus in accordance with claim 2 wherein said control device comprises a sphere at least partially positioned within one of said first and second passageways.

10. An infusion system for administering intravenous fluid to a patient, said infusion system comprising:
    a fluid reservoir; and
    a bifurcated drip chamber coupled in flow communication to said fluid reservoir, said drip chamber comprising a first passageway, a second passageway, a control device, and an inlet coupled in flow communication to said first and second passageways such that fluid discharged from said inlet is received in both first and second passageways when said infusion system is in a first position with said inlet positioned at a higher elevation than said first and second passageways, said control device is in sealing contact against a seat of one of said first and second passageways only when said infusion system is in the first position, said drip chamber rotated to move said control device from said first passageway seat through said first passageway to said second passageway seat through said second passageway for selectively controlling fluid flow out of said first and second passageways, said first passageway for discharging fluid from said drip chamber at a first predetermined rate of flow when said infusion system is in the first position, said second passageway for discharging fluid from said drip chamber at a second predetermined rate of flow when said infusion system is in the first position.

11. An infusion system in accordance with claim 10 further comprising an outlet coupled in flow communication with said drip chamber first and second passageways.

12. An infusion system in accordance with claim 10 wherein said drip chamber is unitary.

13. An infusion system in accordance with claim 10 wherein said drip chamber comprises a sealed system between said inlet and an outlet coupled in flow communication with said first and second passageways, said control valve variably positionable without breaching said sealed system.

14. An infusion system in accordance with claim 13 wherein said drip chamber is bifurcated and comprises a first body portion and a second body portion extending between said outlet and said first and second passageways.

15. An infusion system in accordance with claim 14 wherein said drip chamber first body portion is in flow communication with said first passageway, said second body portion is in flow communication with said second passageway.

16. An infusion system in accordance with claim 14 wherein said drip chamber control device is variably positionable for controlling fluid flow into said first and second body portions by rotating said drip chamber from the first position to a second position, and then by rotating said drip chamber from the second position to the first position.

17. An infusion system in accordance with claim 14 wherein said drip chamber control device is variably positionable for controlling fluid flow into said first and second body portions by inverting said apparatus from the first position into a second position.

18. An infusion system in accordance with claim 10 wherein at least a portion of said drip chamber is transparent.

19. An infusion system in accordance with claim 10 wherein said control device comprises a sphere.

20. A method for administering intravenous fluid to a patient, said method comprising:
   coupling a bifurcated drip chamber including an inlet, a first fluid passageway and a second fluid passageway to a fluid reservoir;
   channeling fluid flow from the fluid reservoir to the drip chamber inlet;
   positioning the drip chamber in a first position wherein fluid flow is channeled from the drip chamber inlet to both the first fluid passageway and a second fluid passageway, wherein the first fluid passageway is configured to discharge fluid therefrom at a first predetermined flow rate, and wherein the second fluid passageway is configured to discharge fluid therefrom at a second predetermined flow rate that is different than the first predetermined flow rate; and
   rotating the drip chamber from the first position to a second position in order to move a control device from a seat of the first fluid passageway via the first fluid passageway to a seat of the second fluid passageway via the second fluid passageway such that the control device is selectively positioned in sealing contact against one seat of said first and second fluid passageways only when the drip chamber is in the first position to control fluid flow discharged from both the first fluid passageway and the second fluid passageway.

21. A method in accordance with claim 20 further comprising discharging the fluid from the drip chamber through an outlet that is in flow communication with the drip chamber first and second fluid passageways.

22. A method in accordance with claim 20 wherein coupling a drip chamber including a first fluid passageway and a second fluid passageway to a fluid reservoir further comprises coupling a unitary drip chamber including a first fluid passageway and a second fluid passageway to the fluid reservoir.

23. A method in accordance with claim 20 wherein coupling a drip chamber that is a sealed system between the inlet and the outlet to the fluid reservoir.

24. A method in accordance with claim 23 wherein positioning a control device to control fluid flow further comprises changing a position of the control valve without breaching the sealed system.

25. A method in accordance with claim 20 wherein positioning a control device to control fluid flow discharged from both the first fluid passageway and the second fluid passageway further comprises positioning a control device between the inlet and the first and second fluid passageways to control fluid flow discharged from both of the first and second fluid passageways.

26. A method in accordance with claim 20 wherein positioning a control device to control fluid flow discharged from the drip chamber inlet further comprises:
   rotating the drip chamber from the first position to the second position; and
   rotating the drip chamber from the second position to the first position such that fluids can be discharged from the drip chamber at the desired predetermined flow rate.

27. A method for fabricating a drip chamber for use in supplying intravenous fluids at a controlled flow rate, said method comprising:
   forming a bifurcated chamber including a first body portion and a second body portion, wherein the first body portion is configured to discharge fluids at a first predetermined flow rate, the second body portion is configured to discharge at a second predetermined flow rate that is different than the first predetermined flow rate;
   coupling the bifurcated chamber to an inlet that is in flow communication with the first and second body portions;
   extending a first fluid passageway between the inlet and the first body portion;
   extending a second fluid passageway between the inlet and the second body portion;
   rotating the drip chamber from a first position to a second position in order to move a control device from a seat of the first fluid passageway via the first fluid passageway to a seat of the second fluid passageway via the second fluid passageway such that the control device is selectively positioned in sealing contact against one seat of said first and second fluid passageways only when the drip chamber is in the first position, the control device controlling fluid flow into the first and second body portions; and
   coupling the bifurcated chamber to an outlet that is in flow communication with the first and second body portions and that is between a patient and the first and second fluid passageways when the drip chamber is in the first position.

28. A method in accordance with claim 27 wherein coupling a control device to the bifurcated chamber further comprises positioning the control device within the fluid passageway such that the control device is variably positionable to control fluid flow into the first and second body portions by rotating the assembly from the first position to the second position and then from the second position to the first position.

29. A method in accordance with claim 27 wherein forming a bifurcated chamber including a first body portion and a second body portion further comprises the bifurcated chamber such that at least a portion of the first body portion and the second body portion are transparent.

30. A method in accordance with claim 20 further comprising visually monitoring the fluid flow supplied to the patient through a transparent portion of the drip chamber.

31. Apparatus in accordance with claim 1 wherein said control device is between said inlet and said first and second passageways.

* * * * *